United States Patent [19]

Weiler et al.

[11] 4,120,957
[45] Oct. 17, 1978

[54] BIS-PHOSPHORAMIDATES

[75] Inventors: Ernest D. Weiler, Ambler; W. David Weir, Levittown; Martha Wolfersberger, Perkasie, all of Pa.

[73] Assignee: Rohm and Haas Company, Philadelphia, Pa.

[21] Appl. No.: 803,181

[22] Filed: Jun. 3, 1977

Related U.S. Application Data

[63] Continuation-in-part of Ser. No. 699,830, Jun. 25, 1976, abandoned.

[51] Int. Cl.$^2$ .......................... A01N 9/36; C07F 9/22
[52] U.S. Cl. ................. 424/204; 260/287 R; 260/295 E; 260/306.8 R; 260/332.2 A; 260/347.3; 260/429 R; 260/429.7; 260/429.9; 260/438.1; 260/439 R; 260/926; 424/200; 424/202; 424/203; 548/378
[58] Field of Search ......................... 424/204; 260/926

[56] References Cited
PUBLICATIONS

Kulka, Canadian Journal of Chemistry, vol. 37, (1959), pp. 525–528.

*Primary Examiner*—Richard L. Raymond
*Attorney, Agent, or Firm*—George W. F. Simmons; Terence P. Strobaugh

[57] ABSTRACT

Substituted phosphoramidates of the general formula:

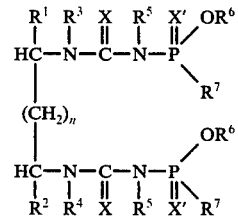

and their pharmaceutically acceptable metal salts and metal salt complexes, compositions containing them, and methods of employing them as anthelmintics are disclosed.

26 Claims, No Drawings

BIS-PHOSPHORAMIDATES

This application is a continuation-in-part of application Ser. No. 699,830, filed June 25, 1976, now abandoned.

The invention relates to phosphoramidates, to compositions containing them and to methods of employing them as anthelmintics.

The compounds of this invention have the following general formula:

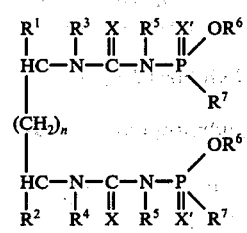

wherein $R^1$ and $R^2$ are the same or different groups selected from hydrogen; $(C_1-C_6)$ alkyl, preferably $(C_1-C_4)$ alkyl; aralkyl of up to 11 and preferably of up to 8 carbon atoms; or $(C_6-C_{10})$ aryl, preferably phenyl; and when $n$ is an integer of 0 to 2, $R^1$ and $R^2$ can be joined together with the alkylene chain to which they are attached to form cyclohexyl; $R^3$ and $R^4$ are the same or different groups selected from hydrogen; ferrocenemethyl; $(C_1-C_6)$ substituted or unsubstituted alkyl, preferably $(C_1-C_4)$ alkyl; wherein the substituent is halo, hydroxy, alkoxy or nitro; $(C_3-C_6)$ alkenyl, preferably $(C_3-C_4)$ alkenyl; alkynyl $(C_3-C_6)$, phenylalkynyl $(C_9-C_{14})$, cycloalkyl, preferably $(C_5-C_7)$ cycloalkyl; $(C_4-C_{12})$ cycloalkylalkyl, preferably $(C_6-C_9)$ cycloalkylalkyl; cycloalkenylalkyl such as 3-cyclohexenylmethyl, aryl such as phenyl, optionally substituted aralkyl or aralkenyl of up to 11 carbon atoms, preferably benzyl, phenethyl or phenylallyl or heterocyclic-alkyl, wherein the alkyl group contains from 1 to 4, preferably from 1 to 2 carbon atoms and the heterocyclic ring contains 5 to 12 members which can include from 1 to 3 hetero atoms such as oxygen, sulfur, nitrogen and the like or any combination of these; $R^5$ is selected from hydrogen, $(C_1-C_6)$ alkyl, preferably $(C_1-C_4)$ alkyl; $(C_3-C_6)$ alkenyl, preferably $(C_3-C_4)$ alkenyl; $(C_3-C_8)$ cycloalkyl, preferably $(C_5-C_7)$ cycloalkyl; $(C_4-C_{12})$ cycloalkylalkyl, preferably $(C_6-C_9)$ cycloalkylalkyl; optionally substituted aralkyl of up to 11 carbon atoms, preferably optionally substituted benzyl or phenethyl; optionally substituted $(C_6-C_{10})$ aryl, preferably optionally substituted phenyl; or heterocyclic-alkyl wherein the alkyl group contains from 1 to 4, preferably from 1 to 2, carbon atoms and the heterocyclic ring contains 5 or 6 members which can include as hetero atoms, oxygen, sulfur or nitrogen or any combination of these wherein the total number of hetero atoms does not exceed 3; $R^6$ is selected from $(C_1-C_6)$ alkyl, preferably $(C_2-C_4)$ alkyl, most preferably ethyl; $(C_2-C_8)$ alkoxyalkyl, preferably $(C_2-C_4)$ alkoxyalkyl; $(C_2-C_4)$ haloalkyl, preferably haloethyl or optionally substituted $(C_6-C_{10})$ aryl, preferably optionally substituted phenyl and most preferably unsubstituted phenyl; $R^7$ is selected from $(C_1-C_5)$ alkoxy, preferably $(C_2-C_4)$ alkoxy, and most preferably ethoxy; $(C_1-C_5)$ alkylthio, preferably $(C_3-C_4)$ alkylthio and most preferably isopropylthio or n-propylthio; optionally substituted $(C_6-C_{10})$ aryloxy, preferably optionally substituted phenoxy, or optionally substituted $(C_6-C_{10})$ arylthio, preferably optionally substituted phenylthio; X is oxygen or sulfur, preferably sulfur; $X'$ is oxygen or sulfur, preferably oxygen; and $n$ is an integer of 0 to 10, provided that when $R^7$ is alkoxy and $n$ is zero, at least one of the $R^1$, $R^2$, $R^3$ and $R^4$ groups is other than hydrogen. The $(CH_2)_n$ group may be substituted with one or two $(C_1-C_4)$ alkyls, preferably methyl, hydroxy, $(C_1-C_4)$ alkoxy or aryl, such as phenyl and the pharmaceutically acceptable metal salts and metal salt complexes thereof.

The metal salts of this invention are the alkali and alkaline earth metal salts of the compounds of Formula I wherein at least one of $R^3$, $R^4$, $R^5$ is a hydrogen atom. The preferred metal salt is the disodium salt.

The metal salt complexes of this invention may be represented by the following formula, which is presented for illustrative purposes only:

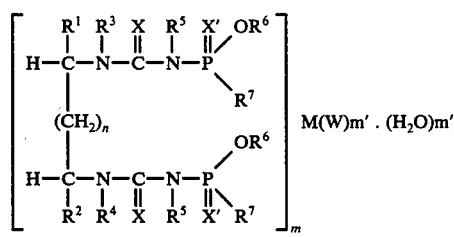

wherein $R^1$, $R^2$, $R^3$, $R^4$, $R^5$, $R^6$, $R^7$, X, $X'$ and $n$ are as defined for Formula I; M is a metal cation which can be selected from groups IIA, IIIA, IB, IIB, VIIB, and VIII of the Periodic Table; W is an anion such as chloride, bromide, iodide, sulfate, bisulfate, phosphate, nitrate, perchlorate, carbonate, bicarbonate, hydroxide, acetate, oxalate, maleate, citrate, and the like; $m$ is an integer of 1-2; $m'$ is an integer of 1-2; and $m''$ is an integer of 0-4.

Among the metal salt complexes depicted by Formula II above, the preferred complexes are those wherein the metal cation is a transition metal such as copper, zinc, nickel, cobalt, tin, cadmium, or manganese; or an alkaline earth metal such as calcium or magnesium, and wherein the anion is chloride, bromide, nitrate, sulfate or hydroxide. The most preferred metal salt complexes are those wherein the metal cation is copper, zinc, nickel, cobalt, tin, cadmium, or manganese.

The preferred compounds of this invention are those wherein $R^5$ is hydrogen, $R^6$ is $(C_2-C_4)$ alkyl, preferably ethyl, and $R^7$ is $(C_2-C_4)$ alkoxy, preferably ethoxy, or $(C_3-C_4)$ alkylthio, preferably isopropylthio or n-propylthio; X is sulfur and $X'$ is oxygen.

The most preferred compounds of this invention possess especially enhanced anthelmintic activity and can be represented by the following formula:

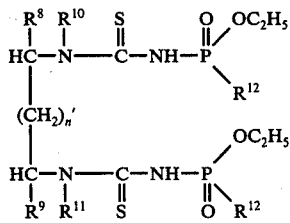

wherein $R^8$ and $R^9$ are the same or different groups selected from hydrogen; $(C_1-C_4)$ alkyl, preferably methyl; and phenyl; or, when n' is an integer of 0 to 2, $R^8$ and $R^9$ can be taken together with the alkylene chain to which they are attached to form cyclohexyl; $R^{10}$ and $R^{11}$ are the same or different groups selected from hydrogen; ($C_1$–$C_4$) alkyl, preferably methyl or ethyl; ($C_6$–$C_9$) cycloalkylalkyl, preferably cyclohexylmethyl; benzyl or phenethyl optionally substituted with from 1 to 3, preferably with from 1 to 2 substituents selected from halo, preferably chloro, nitro and ($C_1$–$C_4$) alkoxy, preferably methoxy or heterocyclicmethyl wherein the heterocyclic ring contains 5 to 12 members and a single hetero atom selected from oxygen, sulfur or nitrogen, preferably a thenyl or pyridylmethyl or quinolylmethyl; $R^{12}$ is ethoxy or ($C_3$–$C_4$) alkylthio, preferably isopropylthio or n-propylthio; and n' is an integer of 0 to 2; provided that when $R^{12}$ is ethoxy and n' is 0, $R^8$, $R^9$, $R^{10}$ and $R^{11}$ are not all both hydrogen and the pharmaceutically acceptable metal salts and metal salt complexes thereof.

As used in the specification and claims, the terms "optionally substituted aralkyl" and "optionally substituted aryl" refer to aralkyl groups as benzyl, phenethyl and naphthylmethylene, and to aryl groups such as phenyl and naphthyl, which can be unsubstituted or substituted with one or more substituents selected from the group consisting of ($C_1$–$C_3$) alkyl, ($C_1$–$C_3$) alkoxy, ($C_1$–$C_3$) alkylthio, di-($C_1$–$C_3$) alkylamino, cyano, nitro and halo, especially chloro. Up to three substituents are preferred, up to two substituents being more preferred.

As used in the specification and claims, the terms "alkyl, alkenyl, alkynyl, alkoxy, alkoxyalkyl, alkylthio, dialkylamino, haloalkyl, aralkyl, cycloalkylalkyl, cycloalkenylalkyl, heterocyclic-alkyl, and the like", include both branched and straight chain groups.

Representative $R^1$ and $R^2$ substituents include, for example, hydrogen, methyl, ethyl, isopropyl, sec-butyl, hexyl, benzyl, phenethyl, α-methylbenzyl, phenylpropyl, naphthylmethylene, phenyl, naphthyl, and the like.

Representative $R^3$ and $R^4$ substituents include, for example, hydrogen, methyl, n-propyl, isobutyl, pentyl, 2-methylpentyl, 2-methyl-2-nitropropyl, hexyl, 2-hydroxyethyl, 2-bromoethyl, 5-hydroxypentyl, allyl, 3-2-(furanyl)allyl, 2-butenyl, 3-methyl-4-pentenyl, hexenyl, cyclopentyl, propargyl, 3-phenylpropargyl, cyclohexyl, cyclooctyl, cyclohexylethyl, cycloheptylmethyl, cyclohexylmethyl, benzyl, 3,5-dimethylbenzyl, 4-methyl-2-methylthiobenzyl, 2-cyanobenzyl, 4-bromo-2-chlorobenzyl, 4-dimethylaminobenzyl, phenyl, methylphenethyl, phenethyl, α-methylbenzyl, 4-nitrophenethyl, cinnamoyl, 2-naphthylmethylene, 3,5-dichloronaphthylmethylene, pyridylethyl; ferrocenemethyl; thiazolylmethyl, pyrazolylmethyl; thienyl, furfuryl, pyridylbutyl and the like.

Representative $R^5$ substituents include those described for $R^3$ and $R^4$ above, as well as additional substituents such as 4-chlorophenyl; 3,4-dichlorophenyl; 2,4,6-trichlorophenyl; 2,3,4,5,6-pentachlorophenyl; 4-bromophenyl; 4-fluorophenyl; 2-methyl-4-methoxyphenyl; 2,5-dimethylphenyl; 2-chloro-4-methylphenyl; 2,4-dichloro-3,5-dimethylphenyl; 4-isopropylphenyl; 4-methylthiophenyl; 4-nitrophenyl; 3-cyanophenyl; naphthyl; 4,5-dichloronaphthyl and the like.

Representative $R^6$ substituents include, for example, methyl, ethyl, isopropyl, n-butyl, sec-butyl, pentyl, neopentyl, hexyl, methoxyethyl, isopropoxymethyl, butoxybutyl, chloroethyl, trichloroethyl, phenyl, 4-methyl-2-nitrophenyl; 3,4-dichlorophenyl; 2-cyano-4-methoxyphenyl; naphthyl; 4-methoxynaphthyl and the like.

Representative $R^7$ substituents include, for example, methoxy, ethoxy, propoxy, sec-butoxy, pentoxy, methylthio, ethylthio, propylthio, isobutylthio, sec-butylthio, pentylthio, phenoxy, 4-chlorophenoxy; 3,5-dichlorophenoxy, phenylthio, 4-methylthiophenyl; 4-methoxyphenylthio, naphthylthio and the like.

Examples of the compounds embraced by this invention include the following:

2,3-bis-[3-(O,O-diethylphosphoryl)thioureido]butane;

5,6-bis-[3-(O,O-diethylphosphoryl)thioureido]decane;

2,3-bis-[3-(O,O-diethylphosphoryl)thioureido]1,4-diphenylhexane;

2,3-bis-[3-(O,O-diethylphosphoryl)thioureido]1,4-diphenyl butane;

1,2-bis-[3-(O,O-diethylphosphoryl)thioureido]cyclohexane;

1,2-bis-[3-(O,ethyl-S-n-propylthiophosphoryl)thioureido]cyclohexane;

1,2-bis-[3-(O,O-diethylphosphoryl)ureido]cyclohexane;

1,2-bis-[3-(O-ethyl-S-n-propylthiophosphoryl)thioureido]-1-phenyl propane;

1,2-bis-[3-(O-ethylOS-n-propylthiophosphoryl)ureido]ethane;

1,2-bis-[1-n-butyl-3-(O,O-diethylphosphoryl)ureido]ethane;

1,2-bis-[1-allyl-3-(O,O-diethylphosphoryl)thioureido]ethane;

1,2-bis-[1-cyclohexyl-3-(O,O-diethylphosphoryl)thioureido]ethane;

1,4-bis-[1-cyclopentylmethyl-3-(O,O-diethylphosphoryl)thioureido]butane;

1,2-bis-[3-(O,O-diethylphosphoryl)-1-(4-methoxybenzyl)thioureido]ethane;

2-[1-benzyl-3-(O,O-diethylphosphoryl)thioureido]-1-[3-(O,O-diethylphosphoryl)-1-methylthioureido]ethane;

1,2-bis-[3-(O,O-diethylphosphoryl)-1-naphthylmethylenethioureido]ethane;

1,2-bis-[3-(O,O-diethylphosphoryl)-1-furfurylthioureido]ethane;

1,2-bis-[3-(O,O-diethylphosphoryl)-3-methylureido]ethane;

1,2-bis-[3-(2-butenyl)-3-(O,O-diethylphosphoryl)thioureido]ethane;

1,2-bis-[3-cyclohexyl-3-(O,O-diethylphosphoryl)thioureido]ethane;

1,2-bis-[3-cyclohexylmethyl-3-(O,O-diethylphosphoryl)thioureido]ethane;

1,2-bis-[3-benzyl-3-(O-methyl-S-n-propylthiophosphoryl)thioureido]ethane;

1,2-bis-{3-[3,4-dichlorophenethyl]-3-[O-ethyl-S-(1-methyl)propylthiophosphoryl]thioureido}butane;

1,2-bis-{3-[O-ethyl-S-methylethylthiophosphoryl]-3-phenylthioureido}ethane;

1,2-bis-[3-(4-bromo-2-chlorophenyl)-3-(O,O-diisopropylphosphoryl)thioureido]ethane;

1,2-bis-[3-(O,O-diethylphosphoryl)-3-(3-pyridylmethyl)thioureido]ethane;

1,2-bis-[1-benzyl-3-(O,O-diethylphosphoryl)-3-methylthioureido]ethane;

2,3-bis-[3-benzyl-3-(O,O-diethylphosphoryl)thioureido]propane;

1,2-bis-[3-(O,O-di-n-butylphosphoryl)thioureido]ethane;

1,2-bis-[3-(O,O-diethoxyethylphosphoryl)thioureido]ethane;

1,2-bis-[3-(O,O-di-2-chloroethylphosphoryl)thioureido]ethane;
2,3-bis-[3-(O,O-diphenylphosphoryl)thioureido]butane;
1,2-bis-[3-(O-phenyl-S-phenylphosphoryl)thioureido]ethane;
1,2-bis-[3-(O,O,4-chlorophenylphosphoryl)thioureido]ethane;
1,2-bis-[3-(3,4-dichlorophenyl)-3-(O,O-diethylphosphoryl)thioureido]ethane;
1,4-bis-[3-(O,O-diethylthiophosphoryl)thioureido]ethane;
1,2-bis-[3-(O-ethyl-S-n-propyldithiophosphoryl)thioureido]ethane;
2,3-bis-[3-(O,O-diethylphosphoryl)thioureido]-1-phenylpropane;
1,2-bis-[1-(3-phenyl)propargyl-3-(O,O-diethylphosphoryl)thioureido]ethane;
1,2-bis-[1-(2-methyl-2-nitro)propyl-3-(O,O-diethylphosphoryl)thioureido]ethane;
1,2-bis-[1-(2-hydroxyethyl)-3-(O,O-diethylphosphoryl)thioureido]ethane;
1,2-bis-[1-(2-bromoethyl)-3-(O,O-diethylphosphoryl)thioureido]ethane;
1,2-bis-[1-phenyl-3-(O,O-diethylphosphoryl)thioureido]-1,2-diphenyl ethane;
1,2-bis-[1-(3,3-diphenyl)propyl-3-(O,O-diethylphosphoryl)thioureido]ethane;
1,3-bis-[1-benzyl-3-(O,O-diethylphosphoryl)thioureido]-2-methyl propane;
1,3-bis-[1-benzyl-3-(O,O-diethylphosphoryl)thioureido]-2-methoxy propane;
1,3-bis-[1-benzyl-3-(O,O-diethylphosphoryl)thioureido]-2-phenyl propane and
1,4-bis-[1-benzyl-3-(O,O-diethylphosphoryl)thioureido]-2,3-diphenyl butane.

The compounds of this invention are prepared by a variety of methods. One method involves reacting the appropriate diamine with the appropriate phosphoroisocyanate or isothiocyanate. This reaction can be represented by the following equation:

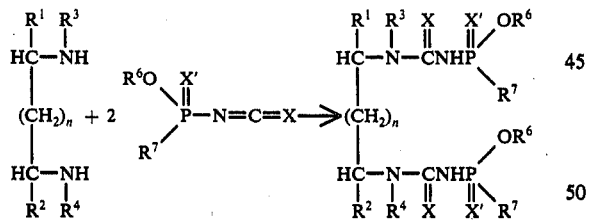

wherein $R^1$, $R^2$, $R^3$, $R^4$, $R^6$, $R^7$, X, X' and n are as defined for Formula I.

The reaction is generally carried out in the presence of an aprotic solvent such as glyme, acetone, acetonitrile, ethyl acetate, butyl acetate, diethyl ether, or mixtures thereof, at a temperature range of about 15° C. to about 120° C., preferably at about 25° C. to about 45° C.

Generally, the preferred molar ratio of diamine to the isocyanate or isothiocyanate is 1:2, but an excess of the isocyanate or isothiocyanate can be used. The desired product can be separated from the reaction mixture by conventional means, such as by fractional crystallization, chromatography, extraction or the like.

Another method for preparing the compounds within the scope of this invention involves reacting the appropriate diamine with the appropriate chloro(thio)carbonylphosphoramidate. This reaction can be represented by the following equation:

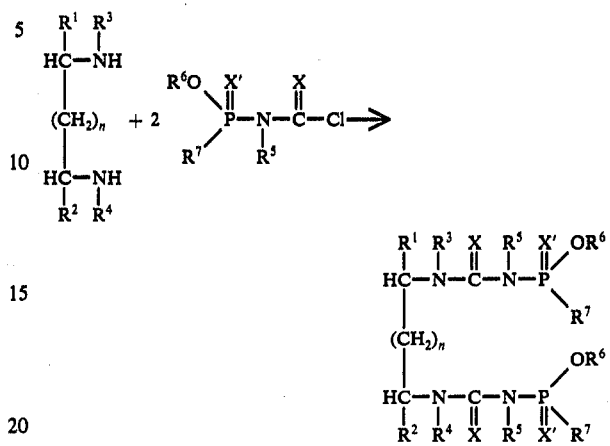

wherein $R^1$, $R^2$, $R^3$, $R^4$, $R^5$, $R^6$, $R^7$, X, X' and n are as defined for Formula I, with the exception that $R^5$ cannot be a hydrogen atom.

This reaction is generally carried out in the presence of an aprotic solvent such as glyme, acetone, acetonitrile, ethyl acetate, butyl acetate, diethyl ether, or mixtures thereof, at a temperature range of from about 15° C. to about 120° C., preferably at about 25° C. to about 45° C. An acid acceptor such as a tertiary amine can be employed as a scavenger in this preparation. Representative acid acceptors include pyridine, trimethylamine, triethylamine and the like. Generally, the preferred ratio of diamine to phosphoramidate is 1:2 but an excess of the phosphoramidate can be used. The desired product can be separated from the reaction mixture by conventional means.

PREPARATION OF DIAMINES

One of the four following procedures can be used to prepare all of the diamines described in this invention:

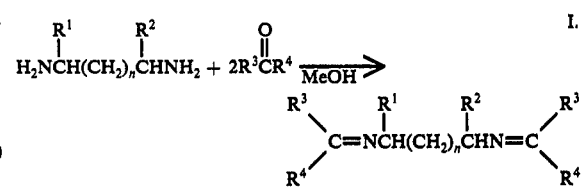

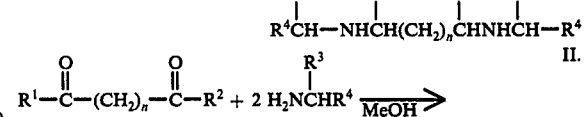

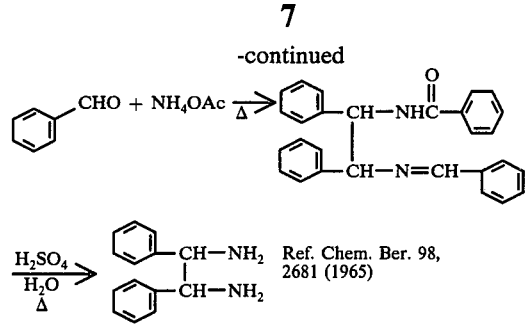

III. Ref. Chem. Ber. 98, 2681 (1965)

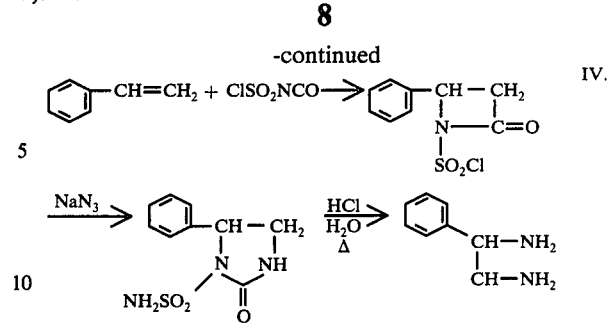

IV. Ref. Ann. 661, 111–117 (1963)

The following Table I illustrates the diamines prepared by one or more of the above methods:

TABLE I $$R^1-CHNH-\underset{R^2-CH-NH}{\overset{R^3\diagdown_{CH}/R^4}{|}}\overset{}{\underset{CH}{\diagup^{R^3}\diagdown R^4}}$$ with Y bridge

| R¹ | R² | R³ | R⁴ | Y | Method | Overall Yield % | M.p. or (b.p./mm Hg)° C. |
|---|---|---|---|---|---|---|---|
| phenyl | phenyl | R³CHR⁴ | =H | — | III | 5 | 116° – 118° |
| H | H | H | 2,3-dichlorophenyl | — | I | 27 | 76° – 77° dec. |
| H | H | H | 2-thienyl | — | I | 24 | — |
| H | H | H | phenyl | (CH₂)₂ | I | 87 | oil |
| H | H | H | benzyl (—CH₂-phenyl) | — | II | 86 | oil |
| H | H | H | 3-pyridyl | (CH₂)₂ | I | 72 | 49° – 55° |
| —(CH₂)₄— | | H | phenyl | — | I | 31 | oil |
| H | H | H | 2-thienyl (S) | — | I | 82 | oil |
| H | H | H | 4-nitrophenyl | — | I | 25 | oil |
| H | H | H | n-C₄H₉n | (CH₂)₂ | I | 88 | oil |
| H | H | H | 4-methoxyphenyl | — | I | 40 | 199° – 208°/ 0.4 mm. |

TABLE I-continued $$\begin{array}{c}R^3\phantom{XX}R^4\\ \diagdown\phantom{X}\diagup\\ CH\\ |\\ R^1-CHNH\\ |\\ Y\\ |\\ R^2-CH-NH\\ |\\ CH\\ \diagup\phantom{X}\diagdown\\ R^3\phantom{XX}R^4\end{array}$$

| $R^1$ | $R^2$ | $R^3$ | $R^4$ | Y | Method | Overall Yield % | M.p. or (b.p./mm Hg)° C. |
|---|---|---|---|---|---|---|---|
| H | H | H | —CH=CHCH$_3$ | — | I | 24 | oil |
| H | H | H | 3-methylquinolinyl | — | I | 15 | 147° – 149° |
| H | H | H | —CH=CH—phenyl | — | I | 43 | oil |
| H | H | H | —CH=CHCH=CHCH$_3$ | — | I | 17 | ~30° |
| CH$_3$ | H | H | phenyl | — | I | 68 | oil |
| H | H | CH$_3$ | —CH$_2$—phenyl | — | I | 94 | oil |
| H | H | H | cyclohexenyl | — | I | 77 | oil |
| H | H | CH$_3$ | —CH$_2$CH$_3$ | — | II | 32 | oil |
| phenyl | H | $R^3$—CH—$R^4$ | =H | — | IV | 11 | b.p. 72° – 83°/0.2 mm. |
| H | H | H | phenyl | —CHOH— | I | 24 | oil |
| H | H | H | ferrocenemethyl | — | I | 63 | 104° – 109° |

The following is a list of known diamines which also may be employed with a reference wherein their preparation is disclosed.

TABLE II $$\begin{array}{c}R^1CHNHR^3\\ |\\ Y\\ |\\ R^2-CH-NHR^4\end{array}$$

| $R^1$ | $R^2$ | $R^3$ | $R^4$ | Y | Reference |
|---|---|---|---|---|---|
| H | H | 2-tetrahydrothiopyranyl | 2-tetrahydrothiopyranyl | —(CH$_2$)$_4$— | CA 70:P 115879 f |
| H | H | H | H | —(CH-phenyl)$_2$ | CA 72:100187 |
| —CH$_3$ | —CH$_3$ | CH$_2$CH$_3$ | CH$_2$CH$_3$ | bond | J. Chem. Soc. (1962) 886–904 |

TABLE II-continued $$\underset{R^2-\overset{|}{C}H-NHR^4}{\overset{R^1CHNHR^3}{\underset{|}{\overset{|}{Y}}}}$$

| R¹ | R² | R³ | R⁴ | Y | Reference |
|---|---|---|---|---|---|
| Ph | Ph | Ph | Ph | " | CA 72:128046y |
| H | H | —CH(CH₃)₂ | —CHCH₂OH<br>\|<br>CH₂CH₃ | " | CA 72:P89762g |
| H | H | CH₃<br>\|<br>—CH₂C—NO₂<br>\|<br>CH₃ | CH₃<br>\|<br>—CH₂C—NO₂<br>\|<br>CH₃ | " | Aust. J. Chem. (1968),21(11), 2797-2800 |
| H | H | —CH₂CH₂OH | —CH₂CH₂OH | bond | CA 75:75962b |
| H | H | —(CH₂)₂CH(φ)₂ | —(CH₂)₂CH(φ)₂ | " | CA 75:P35019v |
| CH₃ | CH₃ | H | H | " | CA 53:11392c |
| H | H | —CH₂Ph | H | H | —CH₂— | J. Org. Chem. (1969) 34(6) 1817-1821 |
| —H | —CH₂Ph | H | H | bond | CA 72:P111473n |
| H | H | —CH₂-C₆H₃(OCH₃)₂ | —CH₂CH₃ | —CH₂CH₂Br | " | J. Med. Chem. (1969) 12(2), 244-253 |

The metal salts of this invention can be prepared by adding an alkali metal or alkaline earth metal hydroxide or hydride to a suspension of the appropriate phosphoramidate in a suitable solvent, stirring the mixture until a solution forms, and then either freeze drying the solution or concentrating it under vacuum at room temperature and drying the residue in a vacuum oven at room temperature.

The metal salt complexes are prepared by reacting, in an aqueous or alcoholic medium, a phosphoramidate of this invention, or alkali metal salt thereof, with a metal cation selected from Groups IIA, IIIA, IB, IIB, VIIB, or VIII of the Periodic Table, collecting the precipitate which forms, and washing and drying the precipitate to give the product.

The starting materials used in the preparation of the compounds of this invention, if not described herein, are known or are readily prepared by methods available to those skilled in the art.

By way of demonstration, the following examples are offered to illustrate this invention and are not to be construed as limitations thereof. The preparation of products depicted in the table headed "Analytical Data" as Examples 3, 6, 7, 8, 10, 14 and 18, has not been included since they are prepared in substantially the same manner as described in the other written examples.

EXAMPLE 1 —
1,2-bis-[3-(O-ethyl-S-isopropylthiophosphoryl)thioureido]ethane

To 0.3 g. (0.005 mole) of ethylenediamine there is added 2.3 g. (0.01 mole) of O-ethyl-S-isopropylthiophosphoryl isothiocyanate (exothermic reaction). To the mixture there is added 5 ml. of acetone and the mixture is allowed to stand at room temperature for several hours. The suspension is vacuum filtered and the filter cake is dried to afford 0.8 g. (31%) of product.

EXAMPLE 2 —
1,2-bis-[1-benzyl-3-(O,O-diethylphosphoryl)thioureido]ethane

To a solution of 1.2 g. (0.005 mole) of N,N'-dibenzyl ethylenediamine in 10 ml. of acetone there is added 2.0 g. (0.01 mole) of O,O-diethylphosphoryl isothiocyanate. The suspension which forms is allowed to stand at room temperature for several hours and is filtered. The filter cake is dried to afford 2.4 g. (75%) of product.

EXAMPLE 4 —
1,2-bis-[1-benzyl-3-(O-ethyl-S-n-propylthiophosphoryl)thioureido]ethane To a solution of 1.2 g. (0.005 mole) of N,N'-dibenzyl ethylenediamine in 5 ml. of acetone there is added 2.25 g. (0.01 mole) of ethoxy n-propylthiophosphoryl isothiocyanate (exothermic reaction). The solution is allowed to stand at room temperature for four hours and the suspension which forms is vacuum filtered. The filter cake is washed with acetone and dried to afford 1.2 g. (35%) of product.

EXAMPLE 5 —
1,2-bis-[3-(O,O-diethylphosphoryl)thioureido]-1,2-diphenyl ethane To a fine suspension of 2.1 g. (0.01 mole) of 1,2-diphenyl ethylenediamine [preparation described in *Berichte* 98, 2681 (1965)] in 100 ml. of acetonitrile there is added 4 g. (0.02 mole) of O,O-diethylphosphoryl isothiocyanate. The mixture is stirred at room temperature for 45 minutes and is vacuum filtered. The filter cake is washed with acetonitrile and dried to afford 1.1 g. (18%) of product.

EXAMPLE 9 —
1,4-bis-[1-benzyl-3-(O,O-diethylphosphoryl)thioureido]butane

To a solution of 21.2 g. (0.2 mole) of benzaldehyde in 50 ml. of methanol there is added, over a period of 5 minutes, 8.8 g. (0.1 mole) of 1,4-diaminobutane (exothermic reaction). The solution is stirred at room temperature for two hours and is cooled to 15° C. To the solution there is added 7.6 g. (0.2 mole) of sodium borohydride over a period of 15 minutes (exothermic reaction with the occurence of considerable foaming). The mixture is stirred at room temperature for 18 hours and is then cautiously poured into 150 ml. of water. The aqueous mixture is extracted with methylene chloride. The methylene chloride extract is dried over magnesium sulfate and concentrated in vacuo affording 23.3 g. (87%) of N,N'-dibenzyl-1,4-diaminobutane as an oil.

To a solution of 1.35 g. (0.005 mole) of the N,N'-dibenzyl-1,4-diaminobutane in 5 ml. of acetone there is added 1.95 g. (0.01 mole) of O,O-diethylphosphoryl isothiocyanate (exothermic reaction). The solution is allowed to stand at room temperature for one hour and the suspension which forms is diluted with 15 ml. of acetone and vacuum filtered. The filter cake is washed with acetone, and ether, and dried to afford 2.1 g. (64%) of product.

EXAMPLE 11 —
1,2-bis-[3-(O,O-diethylphosphoryl)thioureido]propane

To a solution of 4.0 g. (0.02 mole) of O,O-diethylphosphoryl isothiocyanate in 25 ml. of acetone there is added 0.7 g. (0.01 mole) of 1,2-diaminopropane (exothermic reaction). The solution is cooled in dry ice and concentrated in vacuo. The resultant oil is dissolved in ethyl acetate and washed with water. The solution is concentrated in vacuo, dissolved in aqueous base and washed with benzene. The aqueous solution is acidified with concentrated hydrochloric acid and the precipitate which forms is isolated by vacuum filtration. The precipitate is dried to afford 1.4 g. (30%) of product.

EXAMPLE 12 —
1,2-bis-[1-benzyl-3-(O,O-diethylphosphoryl)thioureido]cyclohexane To a solution of 10.6 g. (0.1 mole) of benzaldehyde in 40 ml. of methanol there is added 5.7 g. (0.005 mole) of 1,2-diaminocyclohexane (exothermic reaction). The solution is stirred at room temperature for 18 hours and the suspension which forms is vacuum filtered. The filter cake is dried to afford 6.4 g. (44%) of 1,2-bis-benzylideneamino cyclohexane.

To a suspension of 5 g. (0.0172 mole) of the 1,2-bis-benzylideneamino cyclohexane in 25 ml. of methanol there is added, portionwise, 1.31 g. (0.0345 mole) of sodium borohydride at 10° C. The mixture is stirred at room temperature for 24 hours and is poured into an excess of water. The mixture is extracted with methylene chloride and the extract is dried over magnesium sulfate and concentrated in vacuo to afford 3.2 g. (63%) of the N,N'-dibenzyl-1,2-diaminocyclohexane as an oil.

To a solution of 1.47 g. (0.005 mole) of the N,N'-dibenzyl-1,2-diaminocyclohexane in 5 ml. of acetone there is added 1.95 g. (0.01 mole) of O,O-diethylphosphoryl isothiocyanate (exothermic reaction). The solution is allowed to stand at room temperature for 18 hours and the suspension which forms is vacuum filtered. The filter cake is washed with acetone, and ether, and dried to afford 0.5 g. (14.7%) of product.

EXAMPLE 13 —
1,2-bis-[1-cyclohexylmethyl-3-(O,O-diethylphosphoryl)thioureido]ethane To a solution of 22.4 g. (0.2 mole) of cyclohexane carboxaldehyde in 25 ml. of methanol there is added 6 g. (0.1 mole) of ethylenediamine (exothermic reaction). The solution is stirred at room temperature for one hour and is cooled to 10° C. To the solution there is added portionwise, 7.6 L g. (0.2 mole) of sodium borohydride (exothermic reaction with the occurence of considerable foaming). The mixture is stirred at room temperature for 18 hours and is poured into an excess of water. The aqueous mixture is extracted with methylene chloride. The methylene chloride extract is dried over magnesium sulfate and concentrated in vacuo affording 20.6 g. (82%) of N,N'-dicyclohexylmethyl ethylenediamine as a colorless oil.

To a solution of 1.26 g. (0.005 mole) of the N,N'-dicylohexylmethyl ethylenediamine in 5 ml. of acetone there is added 1.95 g. (0.01 mole) of O,O-diethylphosphoryl isothiocyanate (exothermic reaction). The solution is allowed to stand at room temperature for two hours and the suspension which forms is vacuum filtered. The filter cake is washed with acetone, and ether, and dried to afford 1.8 g. (56%) of product.

EXAMPLE 15 —
1,4-bis-[3-(O,O-diethylphosphoryl)-1-(3-pyridylmethyl)thioureido]butane To a solution of 10.7 g. (0.1 mole) of 3-pyridine carboxaldehyde in 25 ml. of methanol there is added dropwise, 4.4 g. (0.05 mole) of 1,4-diaminobutane (exothermic reaction). The solution is stirred at room temperature for two hours and is cooled to 10° C. To the solution there is added portionwise, 3.8 g. (0.1 mole) of sodium borohydride (exothermic reaction with the occurence of considerable foaming). The mixture is stirred at room temperature for 18 hours and is poured into 200 ml. of water. The solution is extracted with methylene chloride. The extract is dried over magnesium sulfate and concentrated in vacuo affording 9.7 g. (72%) of N,N'-di-(3-pyridylmethyl)-1,4-diaminobutane as an oil. Upon standing, the oil crystallizes, m.p. 49°–55° C.

To a solution of 1.35 g. (0.005 mole) of the N,N'-di(3-pyridylmethyl)-1,4-diaminobutane in 5 ml. of acetone there is added 1.95 g. (0.01 mole) of O,O-diethylphosphoryl isothiocyanate (exothermic reaction). The solution is allowed to stand at room temperature for one hour and the suspension which forms is diluted with 20 ml. of acetone and vacuum filtered. The filter cake is washed with ether and dried to afford 2.2 g. (67%) of product.

EXAMPLE 16 —
1,2-bis-[3-(O,O-diethylphosphoryl)-1-ethylthioureido ethane

To a solution of 1.16 g. (0.01 mole) of N,N'-diethylethylenediamine in 5 ml. of acetone there is added 3.9 g. (0.02 mole) of O,O-diethylphosphoryl isothiocyanate (exothermic reaction). The solution is allowed to stand at room temperature for 18 hours and the suspension which forms is vacuum filtered. The filter cake is washed with acetone, and ether, and dried to afford 2.5 g. (50%) of product.

EXAMPLE 17 —
1,2-bis-[3-(O,O-diethylphosphoryl)-1-(4-nitrobenzyl)-thioureido]ethane To a suspension of 15.1 g. (0.1 mole) of 4-nitrobenzaldehyde in 50 ml. of methanol there is added 3.0 g. (0.05 mole) of ethylenediamine. To facilitate stirring, methanol is added to the thick suspension which forms and the mixture is stirred at room temperature for one hour. The mixture is vacuum filtered and the filter cake dried to afford 15.6 g. (96%) of bis-4-nitrobenzylidene-1,2-diaminoethane, m.p. 116°–200°.

To a suspension of 9.8 g. (0.03 mole) of the N,N'-bis-4-nitrobenzylidene-1,2-diaminoethane in 50 ml. of methanol there is added, portionwise, 2.3 g. (0.06 mole) of sodium borohydride (foaming observed). The suspension is stirred for two hours and is vacuum filtered. The filtrate is poured into an excess of water and the suspension is vacuum filtered to afford 2.6 g. (26%) of N,N'-bis-4-nitrobenzyl-1,2-diaminoethane.

To a solution of 2.6 g. (0.079 mole) of the N,N'-bis-4-nitrobenzyl-1,2-diaminoethane in 25 ml. of acetone there is added 3.1 g. (0.158 mole) of O,O-diethylphosphoryl isothiocyanate. The suspension which forms is diluted with 25 ml. of acetone and is vacuum filtered. The filter cake is washed with acetone and dried to afford 3.1 g. (54%) of product.

EXAMPLE 19 —
Zinc cloride complex of 1,2-bis-[1-benzyl-3-(O,O-diethylphosphoryl)thioureido]ethane To a suspension of 1.26 g. (0.002 mole) of 1.2-bis-[1-benzyl-3-(O,O-diethylphosphoryl)thioureido]ethane in 20 ml. of deionized water there is added 0.32 g. (0.004 mole) of 50% aqueous sodium hydroxide. To the solution which forms there is added 0.272 g. (0.002 mole) of zinc chloride dissolved in 10 ml. of water. The suspension which forms is stirred at room temperature for two hours and is vacuum filtered. The filter cake is washed with water and dried to afford 1.0 g. (72%) of product.

EXAMPLE 20 —
1,2-bis-[1-(2-butenyl)-3-(diethylphosphoryl)thioureido]ethane

To a stirred solution of 6.0 g. (0.0357 mol) g. 1,2-bis-(2-butenylamino)ethane in 25 ml. of acetonitrile is added 14.0 g. (0.0714 mol) g. O,O-diethylphosphoryl isothiocyanate. The mixture is stirred overnight then cooled and filtered. The solid is washed with cold acetonitrile and dried to afford 2.3 L g. (12%) of 1,2-bis-[1-(2-butenyl)-3-(diethylphosphoryl)thioureido]ethane, m.p. 133°–135° C.

EXAMPLE 21 —
1,2-bis-[3-diethylphosphoryl-1-(3-quinolylmethyl)thioureido]ethane To a solution of 2.2 g. (0.0064 mol) g. 1,2-bis-(3-quinolylmethylmethyl)ethane in 25 ml. of acetone is added 3.2 g. (0.016 mol) of O,O-diethylphosphoryl isothiocyanate. The reactants are mixed thoroughly and a mildly exothermic reaction occurs. The mixture is allowed to stand for several hours then filtered. The solid is washed with methanol and dried to afford 1.1 g. (23%) yield of 1,2-bis-[3-diethylphosphoryl-1-(3-quinolylmethyl)thioureido ethane, m.p, 147°–149° C.

EXAMPLE 22 —
1,2-bis-[1-cinnamyl-3-(diethylphosphoryl)thioureido]ethane

To a solution of 2.9 g. (0.01 mol) g. 1,2-bis-(cinnamylamino)ethane in 25 ml. of acetone is added 4.0 g. (0.02 mol) of O,O-diethylphosphoryl isothiocyanate. A mildly exothermic reaction occurs. The reactions are mixed thoroughly and the mixture is allowed to stand overnight then filtered. The solid is washed with acetone and dried to afford 1.7 g. (25%) yield of 1,2-bis-[1-cinnamyl-3-(diethylphosphoryl)thioureido]ethane, m.p. 138°–140° C.

EXAMPLE 23 —
1,2-bis-[3-diethylphosphoryl-1-(2,4-hexadienyl)thioureido]ethane To a solution of 0.9 g. (0.0041 mol) of 1,2-bis-(2,4-hexadienylamino)ethane in 5 ml. of acetone is added 1.6 g. (0.0082 mol) of O,O-diethylphosphoryl isothiocyanate. An exothermic reaction occurs. The reagents are mixed thoroughly then allowed to stand overnight. The solid is collected by filtration, washed with acetone and dried to afford 0.5 g. (20%) yield of 1,2-bis-[3-diethylphosphoryl-1-(2,4-hexadienyl)thioureido]ethane, m.p. 128°–129° C.

EXAMPLE 24 —
1-(3-diethylphosphorylthioureido)-2-(3-diethylphosphoryl-1-methyl)thioureido)ethane To a stirred solution of 2.0 g. (0.01 mol) of O,O-diethylphosphoryl isothiocyanate in 10 ml. of acetone is added 0.4 g. (0.005 mol) of N-methylethylenediamine. The mixture is stirred at room temperature for several hours then diluted with hexane. The sticky precipitate which forms is washed with hexane and ether then crystallized from methanol to afford 0.3 g. (13%) yield of 1-(3-diethylphosphorylthioureido)-2-(3-diethylphosphoryl-1-methyl)thioureido)ethane, m.p. 129°–130° C.

EXAMPLE 25 —
1,2-bis-(1-benzyl-3-diethylphosphorylthioureido)propane

To a stirred solution of 5.0 g. (0.02 mol) of 1,2-bis-benzylaminopropane in 25 ml. acetone is added 8.0 g. (0.04 mol) of O,O-diethylphosphoryl isothiocyanate. The mixture is stirred for one half hour then filtered. The solid is washed with ether and dried to afford 4.2 g. (33%) yield of 1,2-bis-(1-benzyl-3-diethylphosphorylthioureido)propane, m.p. 123°–125° C.

EXAMPLE 26 —
1,2-bis-(3-diethylphosphoryl-1-phenylthioureido)ethane

To a stirred solution of 4.0 g. (0.02 mol) of O,O-diethylphosphoryl isothiocyanate in 5 ml. of acetone is added 2.1 g. (0.1 mol) of dianilinoethane. The mixture is stirred overnight then concentrated. To the residue is added 100 ml. of water plus enough 50% sodium hydroxide to give a strongly basic solution. The mixture is extracted with two 75 ml. portions of methylene chloride and filtered thru celite. The filtrate is cooled and acidified with concentrated hydrochloric acid. The sticky precipitate which forms is crystallized from a mixture of hexane, ether and acetone to afford 0.1 g. (1.6%) yield of 1,2-bis-(3-diethylphosphoryl-1-phenyl-thiouredio)ethane, m.p. 107°–109° C. dec.

EXAMPLE 27 —
1,2-bis-(1-cyclohexenylmethyl-3-diethylphosphorylthioureido)ethane To a stirred solution of 2.5 g. (0.01 mol) of 1,2-bis-(3-cyclohexylmethylamino)ethane in 25 ml. of acetone is added 4.0 g. (0.02 mol) of O,O-diethylphosphoryl isothiocyanate. The mixture becomes warm and within three minutes a precipitate beings to form. The mixture is stirred for one hour then filtered. The solid is washed with methanol and dried to afford 2.3 g. (35%) yield of 1,2-bis-(1-cyclohexenylmethyl-3-diethylphosphorylthioureido)ethane, m.p. 144°–145° C.

EXAMPLE 28 —
1,2-bis-[1-(2-butyl)-3-diethylphosphorylthioureido]ethane

To a stirred solution of 3.4 g. (0.02 mol) of 1,2-bis(2-butylamino)ethane in 25 ml. of acetone is added 7.8 g. (0.04 mol) of O,O-diethylphosphoryl isothiocyanate. An exothermic reaction occurs. Stirring is continued and after 1.5 hour a precipitate begins to form. Stirring is continued for three hours then the solid is collected by filtration to afford 1.7 g. (15%) yield of 1,2-bis-[1-(2-butyl)-3-diethylphosphorylthioureido]ethane, m.p. 119°–120° C.

EXAMPLE 29 —
1,3-bis-(1-benzyl-3-diethylphosphorylthioureido)2-hydroxypropane To a stirred solution of 2.1 g. (0.008 mol) of 1,3-bis-benzylamino-3-hydroxypropane in 25 ml of acetone is added 3.0 g. (0.016 mol) of O,O-diethylphosphoryl isothiocyanate. A mildly exothermic reaction occurs. The mixture is stirred at room temperature for three hours then concentrated. The residue is washed repeatedly with ether and hexane to afford 3.0 g. (56.7%) yield of 1,3-bis-(1-benzyl-3-diethylphosphorylthioureido)-2-hydroxypropane, m.p. 60°–65° C.

EXAMPLE 30 —
1,4-bis-[3-(O,O-diethylphosphoryl)thioureido]butane

To a solution of 0.88 g. (0.01 mol) 1,4-diaminobutane in 20 ml. of acetone there is added 3.9 g. (0.02 mol) of O,O-diethylphosphoryl isothiocyanate (exothermic reaction). The solution is stirred at room temperature for 18 hours and the suspension that forms is vacuum filtered. The filter cake is washed with ether and dried to afford 2.4 g. (50%) yield of 1,4-bis-[3-(O,O-diethylphosphoryl)thioureido]butane, m.p. 155°–157° C. dec.

EXAMPLE 31 — Di-sodium salt-monohydrate of 1,2-bis-[1-methyl-3-(O,O-diethylphosphoryl)thioureido]ethane To a suspension of 9.57 g. (0.02 mol) 1,2-bis-[3-(O,O-diethylphosphoryl)thioureido]ethane in 75 ml. of deionized water, cooled to 5° and under a blanket of nitrogen, there is added 1.65 g. (0.04 mol) of sodium hydroxide pellets (97.1% A.I.). The mixture is stirred at 5° for 1 hour and the solution formed is freeze dried to afford a 7.1 g. (66%) yield of di-sodium salt-monohydrate of 1,2-bis[1-methyl-3-(O,O-diethylphosphoryl)thioureido]ethane, m.p. 85°–110° C.

EXAMPLE 32 —
1,2-bis-[1-(2-ferrocene)methyl-3-(O,O-diethylphosphoryl)thioureido]ethane

Step A -
N,N'-bis-(2-ferrocene)methyl-1,2-diaminoethane

To a solution of 8.56 g. (0.04 mol) ferrocenecarboxaldehyde in 50 ml. of methanol there is added 1.2 g. (0.02 ml) of ethylenediamine (slight exotherm from 23° to 27° C.). The suspension that forms is stirred at room temperature for 2 hours and is cooled to 5° C. To the cooled suspension there is added portionwise 1.52 g. (0.04 mol) of sodium borohydride (slight foaming occurs). The fine suspension that forms is stirred at 10° for one hour and at room temperature overnight. The suspension is poured into 1 l. of water and the oil suspension is extracted with 300 ml. of methylene dichloride. The organic portion is dried over mangesium sulfate and is concentrated in vacuo to afford 5.8 g. (63%) of N,N'-bis-(2-ferrocene)methyl-1,2-diaminoethane, m.p. 104°–109°.

Step B —
1,2-bis-[1-(2-ferrocene)methyl-3-(O,O-diethylphosphoryl)thioureido]ethane To a finely divided suspension of 4.59 g. (0.01 ml) N,N'-bis-(2-ferrocene)methyl-1,2-diaminoethane in 125 ml. of acetone is added 3.9 g. (0.02 ml) of O,O-diethylphosphoryl isothiocyanate (slightly exothermic reaction). The solution that forms is stirred at room temperature for 3 hours and the thick suspension that forms is vacuum filtered. The filter cake is washed with ether and dried to afford 3.6 g. (42%) yield of 1,2-bis-[1-(2-ferrocene)methyl-3-(O,O-diethylphosphoryl)thioureido]ethane.

ANALYTICAL DATA

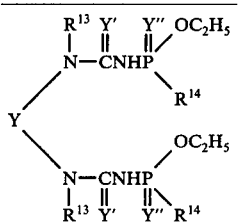

| Compound No. | Y | Y' | Y'' | R¹³ | R¹⁴ | MP(° C) | C | H | N | P | S |
|---|---|---|---|---|---|---|---|---|---|---|---|
| 1 | H₂C—CH₂— (ring) | S | O | H | -SC₃H₇-iso | 138–140 | 33.24 (32.92) | 6.36 (6.33) | 10.87 (10.97) | 12.06 (12.31) | 24.28 (25.11) |
| 2 | H₂C—CH₂— | S | O | —CH₂— | -OC₂H₅ | 138–139 | 49.31 (49.51) | 6.43 (6.40) | 8.97 (8.88) | 9.73 (9.82) | 10.61 (10.17) |
| 3 | H₂C—CH₂— | S | S | H | -OC₂H₅ | 107–108 | 29.80 (29.86) | 6.04 (5.86) | 11.38 (11.61) | 12.69 (12.83) | 26.89 (26.57) |
| 4 | H₂C—CH₂— | S | O | —CH₂ | -SC₃H₇-n | 119–120 dec. | 48.56 (48.67) | 6.29 (6.42) | 8.01 (8.11) | 8.77 (8.97) | — (—) |
| 5 | naphthalene-CH—CH— | S | O | H | -OC₂H₅ | 178–179 dec. | 47.86 (47.82) | 5.93 (6.03) | 9.22 (9.30) | 10.05 (10.27) | 11.30 (11.64) |
| 6 | H₂C—CH₂— | O | O | —CH₂-cyclohexyl | -OC₂H₅ | 149–152 | 52.19 (52.17) | 6.76 (6.74) | 9.13 (9.36) | 10.56 (10.35) | — (—) |
| 7 | H₂C—CH₂— | S | O | —CH₂-(2,3-dichlorophenyl) | -OC₂H₅ | 142–144 | 40.66 (40.63) | 4.70 (4.73) | 7.53 (7.29) | 8.23 (8.06) | 8.32 (8.34) |
| 8 | H₂C—CH₂— | S | O | —CH₂-thienyl | -OC₂H₅ | 134–135 | 41.10 (40.79) | 5.66 (5.52) | 8.71 (8.37) | 9.64 (9.68) | 19.65 (18.95) |
| 9 | H₂C—(CH₂)₂—H₂C— | S | O | —CH₂-phenyl | -OC₂H₅ | 134–136.5 | 51.05 (50.91) | 6.73 (6.69) | 8.51 (8.52) | 9.40 (9.68) | — (—) |
| 10 | H₂C—CH₂— | S | O | —CH₂CH₂-phenyl | -OCH₂H₅ | 128–129 dec. | 51.04 (50.76) | 6.75 (6.72) | 8.51 (8.28) | 9.40 (9.17) | 9.73 (9.76) |
| 11 | H₃C—CH—CH₂— | S | O | H | -OC₂H₅ | 149–150 dec. | 33.61 (33.31) | 6.52 (6.42) | 12.06 (11.80) | 13.33 (13.23) | 13.80 (13.36) |
| 12 | methylcyclohexyl | S | O | —CH₂-phenyl | -OC₂H₅ | 118–121 dec. | 52.62 (52.67) | 6.77 (6.83) | 8.18 (8.04) | 9.05 (8.77) | — (—) |
| 13 | H₂C—CH₂— | S | O | —CH₂-cyclohexyl | -OCH₂H₅ | 142 dec. | 48.59 (48.39) | 8.16 (7.94) | 8.72 (8.96) | 9.64 (9.64) | — (—) |
| 14 | H₂C—CH₂— | S | O | —CH₃ | -OC₂H₅ | 130–131 dec. | 35.14 (35.14) | 6.74 (6.79) | 11.71 (11.90) | 12.95 (12.98) | — (—) |
| 15 | H₂C—(H₂C)₂—H₂C— | S | O | —CH₂-pyridyl | -OC₂H₅ | 124–126 dec. | 47.26 (46.78) | 6.41 (6.49) | 12.72 (12.60) | 9.38 (8.83) | — (—) |
| 16 | H₂C—CH₂— | S | O | —C₂H₅ | -OC₂H₅ | 126.5–127.5 | 37.93 (37.83) | 7.16 (7.41) | 11.06 (11.02) | 12.23 (12.06) | — (—) |
| 17 | H₂C—CH₂— | S | O | —CH₂-(4-nitrophenyl) | -OC₂H₅ | 145–147 | 43.32 (43.05) | 5.32 (5.45) | 11.66 (11.47) | 8.59 (8.36) | 8.90 (8.87) |
| 18 | H₂C—CH₂— | S | O | —CH₂-(4-methoxyphenyl) | -OC₂H₅ | 145–147 | 48.40 (48.14) | 6.98 (6.45) | 8.06 (7.92) | 8.91 (9.11) | 9.23 (8.91) |
| | | | | | | | | | | Zn | Cl |
| 19 | ZnCl₂ complex of compound 2 | | | | | 80–125 | 44.99 (44.26) | 5.52 (5.56) | 8.07 (8.26) | 8.93 (8.74) | 9.42 (9.29) | 0.00 (1.28) |

-continued

ANALYTICAL DATA

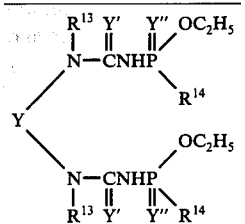

| Compound No. | Y''' | Y' | Y'' | R¹³ | R¹⁴ | MP(°C) | C | H | N | P | S |
|---|---|---|---|---|---|---|---|---|---|---|---|
| 20 | CH₂—<br>\|<br>CH₂— | S | O | —CH₂CH=<br>CHCH₃ | -OC₂H₅ | 133–135 | 42.99<br>(42.99) | 7.23<br>(7.54) | 10.03<br>(10.09) | 11.09<br>(10.80) | 11.48<br>(11.8) |
| 21 | CH₂—<br>\|<br>CH₂— | S | O | —CH— (indoline) | -OC₂H₅ | 147–149 | 52.44<br>(52.29) | 5.79<br>(5.96) | 11.47<br>(11.34) | 8.45<br>(8.40) | 8.75<br>(8.46) |
| 22 | CH₂—<br>\|<br>CH₂— | S | O | —CH₂CH=<br>CH—⌬ | -OC₂H₅ | 138–140 | 52.76<br>(52.96) | 6.51<br>(6.67) | 8.31<br>(8.10) | 9.07<br>(8.97) | 9.39<br>(10.06) |
| 23 | CH₂—<br>\|<br>CH₂— | S | O | —CH₂CH=<br>CHCH=<br>CHCH₂ | -OC₂H₅ | 128–129 | 47.19<br>(47.47) | 7.28<br>(7.51) | 9.18<br>(9.21) | 10.14<br>(9.22) | 10.50<br>(11.10) |
| 24 | CH₂—<br>\|<br>CH₂— | S | O | N—H<br>N'—CH₃ | -OC₂H₅ | 129–130 | 33.61<br>(33.72) | 6.52<br>(6.68) | 12.06<br>(12.03) | 13.34<br>(13.53) | 3.80<br>(14.12) |
| 25 | CH₃<br>\|<br>CH—<br>\|<br>CH₂ | S | O | —CH₂—⌬ | -OC₂H₅ | 123–125 | 50.29<br>(50.00) | 6.58<br>(6.60) | 8.69<br>(8.66) | 9.61<br>(9.32) | 9.94<br>(10.13) |
| 26 | CH₂—<br>\|<br>CH₂— | S | O | —⌬ | -OC₂H₅ | 107–109 | 47.83<br>(48.18) | 6.02<br>(6.02) | 9.30<br>(9.30) | —<br>(—) | —<br>(—) |
| 27 | CH₂—<br>\|<br>CH₂— | S | O | —CH₂—⌬ (cyclohexene) | -OC₂H₅ | 144–145 | 48.89<br>(48.71) | 7.57<br>(7.56) | 8.77<br>(8.73) | 9.70<br>(9.64) | 10.04<br>(9.97) |
| 28 | CH₂—<br>\|<br>CH₂— | S | O | CH₃<br>\|<br>—CH<br>CH₂<br>CH₃ | -OC₂H₅ | 119–120 | 42.69<br>(42.39) | 7.88<br>(7.99) | 9.95<br>(9.77) | 11.01<br>(—) | 11.40<br>(—) |
| 29 | CH₂—<br>\|<br>HOCH<br>\|<br>CH₂ | S | O | —CH₂—⌬ | -OC₂H₅ | 60–65 | 49.08<br>(49.58) | 6.41<br>(16.64) | 8.48<br>(8.19) | 9.38<br>(9.20) | 9.71<br>(8.60)<br>(8.24) |
| 30 | —(CH₂)₄— | S | O | H | -OC₂H₅ | 155–157 dec. | 35.14<br>(35.96) | 6.74<br>(5.60) | 11.71<br>(12.68) | 12.95<br>(12.24) | —<br>(—) |
| 31 | disodium salt of Example 14 | | | | | 85–110 | 31.11<br>(30.80) | 5.97<br>(5.80) | 10.37<br>(10.53) | 11.46<br>(11.23) | H₂O 3.33<br>(3.98) |
| 32 | CH₂—<br>\|<br>CH₂— | S | O | ferro-<br>cenene-<br>methyl | -OC₂H₅ | 120–124 | 48.12<br>(48.58) | 5.94<br>(5.94) | 6.60<br>(6.58) | 7.30<br>(6.88) | |

The present compounds and the metal salts and metal salt complexes thereof (hereinafter collectively referred to as compounds) are active, both therapeutically and prophylactically as anthelmintics. They are especially effective against pinworms and tapeworms.

Certain compounds of this invention are also active as insecticides, acaricides, plant growth regulators, herbicides, and/or as phytopathogenic fungicides.

ANTHELMINTIC TESTING PROCEDURE

The parasites used in the screening program are *Syphacia obvelata* and *Aspicularia tetraptera* (pinworms), *Hymenolepis nana* (dwarf tapeworm), *Nematospiroides dibius* (trichostrongyloid), *Ascaris suum* (ascarid) and *Schistosoma mansoni* (fluke). The host animals are mice.

Infection with parasites and testing procedures are performed in the following manner: Four weeks prior to the initiation of the test, the mice are injected intraperitoneally with a 100–150 cercariae (immature *S. mansoni* larvae). One week prior to the test, the mice are exposed to a natural infection of pinworms. A diet of the test compounds homogenously mixed in ground meal (Lab-Blox) is prepared and placed in feeders where the mice could feed ad libitum for a 13 day period. One day after the test diet has been fed to the mice, they are infected with tapeworm eggs and trichostrongyloid larvae (hookworm) by oral intubation into the esophagus (gavage). On the sixth day after the test date, they are infested with ascarid eggs by gavage. One the eleventh, twelfth and thirteenth day after the test diet has been initiated, the mice are given, by gavage, a 0.2 ml. oral dosage containing the compound to be tested and one-half percent suspensions of methyl cellulose in water once daily for three days. The test is terminated on the fourteenth day and the mice necropsied. Efficacy of the test compounds, recorded as percent reduction, is determined from results based on comparisons of infections between treated experimental groups (4 mice per group) and nontreated control groups.

The compounds of this invention are readily formulated into a variety of suitable pharmaceutical dosage forms such as boluses, tablets, pills, powders, capsules, liquids, suspensions, pastes and gels. The dosage forms are prepared using pharmaceutically acceptable carriers and known methods of formulation and manufacture. In the veterinary field, such formulations can be administered in the animals' food.

Representative solid carriers conveniently available and satisfactory for pharmaceutically acceptable unit dosage formulations include corn starch, powdered lactose, powdered sucrose, talc, stearic acid, magnesium stearate, finely divided bentonite, and the like. The active agent can be mixed with a carrier in varying proportions from, for example, about 0.001 percent by weight in animal food to about 90 or 95 percent or more in a pill or capsule. In the latter form, one might use more carrier than sufficient to bind the particles of the active compound.

The compounds of this invention should be mixed with animal feeds in a way that will avoid degradation of the compound.

In general, the compounds can be formulated into stable powders or granules for mixing in an amount of feed for a single feeding or enough feed for one day and thus obtain therapeutic efficacy without complication. For prepared and stored feed or feed premixes, a recommended practice is to coat a granular formulation to protect and preserve the active ingredient.

A solid diluent carrier need not be a homogeneous entity, but can be a mixture of different diluent carriers. Moreover, formulations with a solid carrier can include small proportions of adjuvants such as water, alcohols, protein solutions and suspensions, edible oils, sugar solutions, and organic adjuvants such as propylene glycols, sorbitol, glycerol, diethylcarbonate, and the like.

Liquid formulations can also be used. Representative liquid formulations include aqueous (including isotonic saline) suspensions, oil solutions and suspensions, and oil in water emulsions. Aqueous suspensions are obtained by dispersing the active compound in water, preferably including a suitable surface-active dispersing agent such as a cationic, anionic, or nonionic surface-active agent.

Representative suitable surface-active agents are polyoxyalkylene derivatives of fatty alcohols and of sorbitan esters, and glycerol and sorbitan esters of fatty acids. Various dispersing or suspending agents can also be included. Representative dispersing agents are synthetic and natural gums, tragacanth, acacia, alginate, dextran, gelatin, sodium carboxymethylcellulose, methylcellulose, polyvinylpyrrolidone, and the like. The proportion of the active compound in the aqueous suspensions of the invention can vary from about 1 percent to about 20 percent or more.

Oil solutions are prepared by mixing the active compound and an oil, e.g., an edible oil such as cottonseed oil, peanut oil, coconut oil, modified soybean oil, and sesame oil. Usually, solubility in oil will be limited and oil suspensions can be prepared by mixing additional finely divided compound in the oil.

Oil in water emulsions are prepared by mixing and dispersing an oil solution or suspension of the active compound in water, preferably aided by surface-active agents and dispersing or suspending agents as indicated above.

In general, the formulations of this invention are administered to animals so as to achieve therapeutic or prophylactic levels of the active compound. The exact concentration of compound administered can depend upon numerous factors such as the type of animal being treated, its age, weight, and tolerance, the time of administration, and the type and number of helminths present. Thus, dosage rates can vary from about 1 mg. to about 800 mg. per kg. of body weight. A preferred range of dosage rates is from about 5 mg. to about 400 mg. per kg. of body weight. In particular, for use against species of both pinworms and tapeworms, a compound is most desirably administered between about 12 and about 100 mg./kg. For use against tapeworms only, the effective dose can be somewhat lower, e.g., about 3 to about 50 mg./kg.

The concentration of active compound in the formulation selected for administration is, in many situations, not critical. One can administer a large quantity of a formulation having a relatively low concentration and achieve the same therapeutic or prophylactic dosage as a relatively small quantity of a relatively more concentrated formulation. More frequent small dosages will likewise give results comparable to one large dose. Unit dosage forms in accordance with this invention can have anywhere from less than 1 mg. to about 500 g. of active compound per unit.

If desired, the solid unit dosage forms of this invention including pellets and granules can be coated so as to provide timed release in the digestive system of animals. Such laminated or enteric coated forms are prepared by appropriately applying to a pill or bolus, a polymeric acid or a mixture of a polymeric acid with shellac, and cetyl alcohol, cellulose acetate, or styrene maleic acid copolymer.

By way of illustration, Examples I and II present suitable formulations for tablets and chewable tablets, respectively.

EXAMPLE I

A tablet of the following composition is formulated:

| | |
|---|---|
| Active Compound | 220 mg. |
| Lactose | 53.23 mg. |
| Magnesium Aluminum Silicate Gel | 2.24 mg. |
| Starch | 13.13 mg. |
| Calcium Stearate | 0.65 mg. |
| Microcrystallin Cellulose | 35.75 mg. |
| TOTAL | 325 mg. |

A granulation, contaning water by the use of magnesium aluminum silicate and starch in the form of pastes, is tableted to form flat level, double or quarter scored, uncoated tablets of 6 to 9 S.C.A. hardness. The appropriate number (and fraction of tablets) is administered to the host.

EXAMPLE II

An alternate formulation is in the form of a palatable chewable tablet. Each chewable tablet contains:

| | |
|---|---|
| Active Compound | 110 mg. |
| Dried Fish Meal | 1027 mg. |

| -continued | |
|---|---|
| Dried Liver Powder, Bovine | 1027 mg. |
| Soybean Oil Meal | 97 mg. |
| Cane Sugar | 239 mg. |
| TOTAL | 2500 mg. |

The exact concentration of the compound to be employed in the compositions can vary, provided that a sufficient amount of the composition is ingested by the animal so as to provide the required dosage of active agent. The compounds of this invention are useful for killing and controlling parasitic worms in ovines, bovines, equines, swine, birds, canines, felines, fish, human beings, and other animals.

The compounds of this invention can be utilized as the sole anthelmintic agent or they can be employed in conjunction with other anthelmintics. Appropriate dosage forms containing a plurality of anthelmintically active compounds are accordingly contemplated by the present invention.

Many variations of this invention are possible without departing from the spirit or scope thereof.

What is claimed is:

1. A compound of the formula:

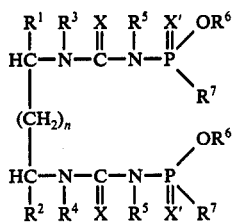

wherein $R^1$ and $R^2$ are the same or different groups selected from hydrogen, ($C_1$-$C_6$) alkyl, aralkyl of up to 11 carbon atoms or ($C_6$-$C_{10}$) aryl; and when $n$ is an integer of 0 to 2, $R^1$ and $R^2$ can be joined together with the alkylene chain to which they are attached to form cyclohexyl; $R^3$ and $R^4$ are the same or different groups selected from hydrogen, unsubstituted ($C_1$-$C_6$) alkyl, ($C_1$-$C_6$) haloalkyl, ($C_1$-$C_6$) hydroxy alkyl, ($C_1$-$C_6$) alkoxyalkyl, ($C_1$-$C_6$) nitroalkyl, ($C_3$-$C_6$) alkenyl, ($C_3$-$C_6$) alkynyl, phenylalkynyl, ($C_3$-$C_8$) cycloalkyl, ($C_4$-$C_{12}$) cycloalkylalkyl, cycloalkenylalkyl, ferrocenemethyl, aryl, optionally substituted aralkyl or aralkenyl of up to 11 carbon atoms, wherein the substituent is one or more substituents selected from ($C_1$-$C_3$) alkyl, ($C_1$-$C_3$) alkoxy, ($C_1$-$C_3$) alkylthio, di-($C_1$-$C_3$) alkylamino, cyano, nitro or halo, $R^5$ is selected from hydrogen, ($C_1$-$C_6$) alkyl, ($C_3$-$C_6$) alkenyl, ($C_3$-$C_8$) cycloalkyl, ($C_4$-$C_{12}$) cycloalkylalkyl, optionally substituted aralkyl of up to 11 carbon atoms, optionally substituted ($C_6$-$C_{10}$) aryl wherein the substituent is one or more substituents selected from ($C_1$-$C_3$) alkyl, ($C_1$-$C_3$) alkoxy, ($C_1$-$C_3$) alkylthio, di-($C_1$-$C_3$) alkylamino, cyano, nitro or halo, $R^6$ is selected from ($C_1$-$C_4$) alkyl; ($C_2$-$C_8$) alkoxyalkyl, ($C_2$-$C_4$) haloalkyl or optionally substituted ($C_6$-$C_{10}$) aryl wherein the substituent is one or more substituents selected from ($C_1$-$C_3$) alkyl, ($C_1$-$C_3$) alkoxy, ($C_1$-$C_3$) alkylthio, di-($C_1$-$C_3$) alkylamino, cyano, nitro or halo; $R^7$ is selected from ($C_1$-$C_5$) alkoxy, ($C_1$-$C_5$) alkylthio, optionally substituted ($C_6$-$C_{10}$) aryloxy or optionally substituted ($C_6$-$C_{10}$) arylthio wherein the substituent is one or more substituents selected from ($C_1$-$C_3$) alkyl, ($C_1$-$C_3$) alkoxy, ($C_1$-$C_3$) alkylthio, di-($C_1$-$C_3$) alkylamino, cyano, nitro or halo; X is oxygen or sulfur; X' is oxygen or sulfur and $n$ is an integer of 0 to 10 provided that when $R^7$ is alkoxy and $n$ is 0, at least one of the $R^1$, $R^2$, $R^3$ and $R^4$ groups is other than hydrogen, the $(CH_2)_n$ group may be substituted with alkyl, hydroxy, alkoxy or aryl and the pharmaceutically acceptable metal salts and metal salt complexes thereof.

2. The compound of claim 1 wherein $R^1$ and $R^2$ are the same or different groups selected from hydrogen, ($C_1$-$C_4$) alkyl, aralkyl of up to 8 carbon atoms, or phenyl; $R^3$ and $R^4$ are the same or different groups selected from hydrogen, ($C_1$-$C_4$) alkyl, ($C_3$-$C_4$) alkenyl, ($C_3$-$C_6$) alkynyl, ($C_5$-$C_7$) cycloalkyl, ($C_6$-$C_9$) cycloalkylalkyl, phenyl, optionally substituted benzyl or phenylallyl or phenethyl; wherein the substituent is one or more substituents selected from ($C_1$-$C_3$) alkyl, ($C_1$-$C_3$) alkoxy, ($C_1$-$C_3$) alkylthio, di-($C_1$-$C_3$) alkylamino, cyano, nitro or halo; $R^5$ is selected from hydrogen, ($C_1$-$C_4$) alkyl, ($C_3$-$C_4$) alkenyl, ($C_5$-$C_7$) cycloalkyl, ($C_6$-$C_9$) cycloalkylalkyl, optionally substituted benzyl or phenethyl, optionally substituted phenyl; wherein the substituent is one or more substituents selected from ($C_1$-$C_3$) alkyl, ($C_1$-$C_3$) alkoxy, ($C_1$-$C_3$) alkylthio, di-($C_1$-$C_3$) alkylamino, cyano, nitro or halo; $R^6$ is selected from ($C_2$-$C_4$) alkyl, ($C_2$-$C_4$) alkoxyalkyl, haloethyl or optionally substituted phenyl wherein the substituent is one or more substituents selected from ($C_1$-$C_3$) alkyl, ($C_1$-$C_3$) alkoxy, ($C_1$-$C_3$) alkylthio, di-($C_1$-$C_3$) alkylamino, cyano, nitro or halo; $R^7$ is selected from ($C_2$-$C_4$) alkoxy, ($C_3$-$C_4$) alkylthio, optionally substituted phenoxy, or optionally substituted phenylthio; wherein the substituent is one or more substituents selected from ($C_1$-$C_3$) alkyl, ($C_1$-$C_3$) alkoxy, ($C_1$-$C_3$) alkylthio, di-($C_1$-$C_3$) alkylamino, cyano, nitro or halo; X is sulfur; X' is oxygen or sulfur; and $n$ is an integer of 0 to 10 provided that when $R^7$ is alkoxy and $n$ is 0, at least one of $R^1$, $R^2$, $R^3$ and $R^4$ is other than hydrogen, the $(CH_2)_n$ group may be substituted with one or two methyl, hydroxy, ethoxy or phenyl groups and the pharmaceutically acceptable metal salts and metal salt complexes thereof.

3. The compound of claim 2 wherein $R^5$ is hydrogen, $R^6$ is ($C_2$-$C_4$) alkyl, and $R^7$ is ($C_2$-$C_4$) alkoxy or a ($C_3$-$C_4$) alkylthio and the pharmaceutically acceptable metal salts and metal salt complexes thereof.

4. The compound of claim 3 of the formula:

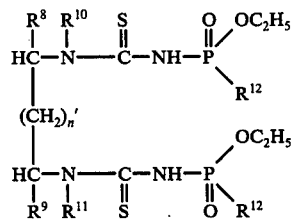

wherein $R^8$ and $R^9$ are the same or different groups selected from hydrogen, ($C_1$-$C_4$) alkyl or phenyl; or when $n'$ is an integer of 0 to 2, $R^8$ and $R_9$ can be taken together with the alkylene chain to which they are attached to form cyclohexyl; $R^{10}$ and $R^{11}$ are the same or different groups selected from hydrogen, ($C_1$-$C_4$) alkyl, cycloalkylalkyl and benzyl or phenethyl optionally substituted with 1 to 3 substituents selected from the group consisting of halo, nitro, and ($C_1$-$C_4$) alkoxy; $R^{12}$ is ethoxy or ($C_3$-$C_4$) alkylthio; and $n'$ is an integer of 0 to 2, provided that when $R^{12}$ is ethoxy and $n'$ is 0, $R^{10}$ and $R^{11}$ are not both hydrogen, and $n'$ is 1 to 2, $(CH_2)_n$ is substituted with 1 or 2 ($C_1$-$C_4$) alkyls, and the pharmaceutically acceptable metal salts and metal salt complexes thereof.

5. The compound of claim 4 wherein $R^8$ and $R^9$ are the same or different groups selected from hydrogen, methyl or phenyl; or when $n$ is 0, $R^8$ and $R^9$ can be joined together with the alkylene chain to which they are attached to form cyclohexyl; $R^{10}$ and $R^{11}$ are the same and are selected from hydrogen, methyl, ethyl, cyclohexylmethyl and optionally substituted benzyl or phenethyl, wherein the substituent is selected from chloro, nitro or methoxy; $R^{12}$ is ethoxy, isopropylthio, or n-propylthio; and $n'$ is an integer of 0 to 2 provided that when $R^{12}$ is ethoxy and $n'$ is 0, $R^{10}$ and $R^{11}$ are not both hydrogen, and the pharmaceutically acceptable metal salts and metal salt complexes thereof.

6. The compound of claim 5 named 1,2-bis-[1-benzyl-3-(0,0-diethylphosphoryl)thioureido]ethane.

7. The compound of claim 5 named 1,4-bis-[1-benzyl-3-(0,0-diethylphosphoryl)thioureido]butane.

8. The compound of claim 5 named 1,2-bis-[1-benzyl-3-(0,0-diethylphosphoryl)thioureido]cyclohexane.

9. The compound of claim 5 named 1,2-bis-[1-methyl-3-(0,0-diethylphosphoryl)thioureido]ethane.

10. An anthelmintic composition for oral administration comprising an anthelmintically effective amount of a compound, metal salt, or metal salt complex, of claim 1 and a pharmaceutically acceptable carrier.

11. An anthelminitic composition for oral administration comprising an anthelmintically effective amount of a compound, metal salt, or metal salt complex, of claim 2 and a pharmaceutically acceptable carrier.

12. An anthelmintic composition for oral administration comprising an anthelmintically effective amount of a compound, metal salt, or metal salt complex, of claim 3 and a pharmaceutically acceptable carrier.

13. An anthelmintic composition for oral administration comprising an anthelminitically effective amount of a compound, metal salt, or metal salt complex, of claim 4 and a pharmaceutically acceptable carrier.

14. An anthelmintic composition for oral administration comprising an anthelmintically effective amount of a compound of claim 5 and a pharmaceutically acceptable carrier.

15. A method for controlling helminth infection in a host animal which comprises administering to the animal an anthelmintically effective amount of a composition according to claim 10.

16. A method for controlling a helminth infection in a host animal which comprises administering to the animal an anthelmintically effective amount of a composition according to claim 11.

17. A method for controlling a helminth infection in a host animal which comprises administering to the animal an anthelmintically effective amount of a composition according to claim 12.

18. A method for controlling a helminth infection in a host animal which comprises administering to the animal an anthelmintically effective amount of a composition according to claim 13.

19. A method for controlling a helminth infection in a host animal which comprises administering to the animal an anthelmintically effective amount of a composition according to claim 14.

20. The method of claim 15 wherein the host animal is a mammal.

21. The method of claim 20 wherein the helminths are tapeworms or pinworms.

22. The method of claim 15 wherein the host animal is a swine.

23. The method of claim 15 wherein the host animal is an equine.

24. The method of claim 15 wherein the host animal is a feline.

25. The method of claim 15 wherein the host animal is a canine.

26. The method of claim 15 wherein the host animal is a human being.

* * * * *